United States Patent
Ogawa et al.

(10) Patent No.: US 7,549,341 B2
(45) Date of Patent: Jun. 23, 2009

(54) METHOD OF MAINTAINING A MULTITUBULAR REACTOR

(75) Inventors: Yasushi Ogawa, Yokkaichi (JP); Shuhei Yada, Yokkaichi (JP); Yoshiro Suzuki, Yokkaichi (JP); Kenji Takasaki, Yokkaichi (JP); Kimikatsu Jinno, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 309 days.

(21) Appl. No.: 11/597,939

(22) PCT Filed: Oct. 25, 2004

(86) PCT No.: PCT/JP2004/016173

§ 371 (c)(1),
(2), (4) Date: Jan. 30, 2007

(87) PCT Pub. No.: WO2005/115605

PCT Pub. Date: Dec. 8, 2005

(65) Prior Publication Data

US 2008/0271539 A1    Nov. 6, 2008

(30) Foreign Application Priority Data

May 31, 2004  (JP) ............................. 2004-161314

(51) Int. Cl.
*G01L 13/00* (2006.01)
(52) U.S. Cl. .......................................... 73/716; 73/736
(58) Field of Classification Search ................ 73/716, 73/736
See application file for complete search history.

(56) References Cited

U.S. PATENT DOCUMENTS

| | | | |
|---|---|---|---|
| 6,694,802 B1 * | 2/2004 | Comardo | 73/37 |
| 6,981,422 B1 * | 1/2006 | Comardo | 73/756 |
| 2007/0148062 A1 * | 6/2007 | Haas et al. | 422/196 |

FOREIGN PATENT DOCUMENTS

| | | |
|---|---|---|
| JP | 5-31351 | 2/1993 |
| JP | 6-296854 | 10/1994 |
| JP | 9-141084 | 6/1997 |
| JP | 10-277381 | 10/1998 |
| JP | 2852712 | 2/1999 |
| JP | 11-333282 | 12/1999 |
| JP | 2000-185227 | 7/2000 |
| JP | 2003-206244 | 7/2003 |

* cited by examiner

*Primary Examiner*—Andre J Allen
(74) *Attorney, Agent, or Firm*—Oblon, Spivak, McClelland, Maier & Neustadt, P.C.

(57) ABSTRACT

The object of this invention is to provide a method of maintaining a multi-tubular reactor which can ensure the uniformity of states of reaction in the reaction tubes in the multi-tubular reactor.

This invention is a method of maintaining a multi-tubular reactor in good condition by selecting a part of reaction tubes in a multi-tubular reactor at random, measuring a differential pressure occurring in each reaction tube when passing gas therethrough, separating any reaction tube showing an abnormal differential pressure as compared with the average of differential pressures in reaction tubes packed with an fresh catalyst of the same kind, giving adequate treatment to the separated reaction tube and returning it into the reactor with any other selected reaction tube falling within a normal range.

10 Claims, No Drawings

METHOD OF MAINTAINING A MULTITUBULAR REACTOR

TECHNICAL FIELD

This invention relates to a method of maintaining a multi-tubular reactor containing a multiplicity of reaction tubes packed with a catalyst and used for carrying out a gas-phase catalytic reaction, while supplying a reactant raw material gas, and relates more particularly to a method of maintaining a multi-tubular reactor in good condition by selecting a part of reaction tubes in a multi-tubular reactor, measuring a differential pressure in each reaction tube, separating any reaction tube showing an abnormal differential pressure as compared with the average of differential pressures in reaction tubes packed with an fresh catalyst of the same kind (average initial differential pressure) and giving-adequate treatment to the separated reaction tube.

BACKGROUND ART

A gas-phase catalytic oxidation reaction by which propane, propylene or isobutylene is, for example, oxidized with molecular oxygen or a gas containing molecular oxygen in the presence of a composite oxidation catalyst to produce (meth)acrolein or (meth)acrylic acid is a typical gas-phase catalytic reaction using a multi-tubular reactor to which this invention pertains.

A multi-tubular reactor used for the reaction of propylene, etc. contains several thousand to several tens of thousand reaction tubes and it is desirable that as uniform a differential pressure as possible act on the reaction tubes at the time of the reaction. If the reaction tubes differ in differential pressure from one another, a problem arises in that a different amount of gas flows from one reaction tube to another and makes a different state of reaction from one reaction tube to another even in one and the same reactor.

The reaction temperature of a reactor is determined in accordance with the average of states of reaction in all the reaction tubes and in the case of, for example, a former-stage reactor intended for the oxidation reaction of propylene, the temperature of the heat medium to be used is usually determined in accordance with the average of the conversion rates of propylene in all the reaction tubes, since the conversion rate of propylene differs from one reaction tube to another. Thus, all of the reaction tubes are not operated under the optimum conditions.

It is important for the safe operation of a multi-tubular reactor to unify the states of reaction in its reaction tubes, or unify their differential pressures, since the state of reaction differing from one reaction tube to another presents the problems as stated below.

(1) At the same reaction temperature, a reaction tube having a large amount of gas shows a low conversion rate of a raw material and a low yield. At the same reaction temperature, a reaction tube having a small amount of gas, on the other hand, shows an excessive reaction with a lot of side reactions and a low selectivity.

(2) Moreover, a reaction tube having a small amount of gas shows a deficiency of oxygen at its outlet, causing not only the deterioration of a catalyst, but also its coking, in addition to the occurrence of the excessive side reactions and the lowering of selectivity as stated above.

(3) The difference in the state of reaction from one reaction tube to another leads to a different level of deterioration of the catalyst and a shortening of catalyst life as a whole.

However, the reaction tubes showing an abnormal differential pressure, as thereby causing coking, are scattered in a multi-tubular reactor containing several thousand to several tens of thousand reaction tubes as mentioned before and exist without showing any tendency at those sites in the reactor which cannot be explained by the flow of reaction gas or the flow of a heat medium.

There is no technique aimed at unifying the differential pressures of the reaction tubes in a multi-tubular reactor, as far as the inventors of this invention know.

DISCLOSURE OF THE INVENTION

In view of the problems as stated above, this invention has been made to provide a method of maintaining a multi-tubular reactor for unifying the differential pressures of reaction tubes as far as possible when the reaction tubes in the multi-tabular reactor, packed with a catalyst carry out a gas-phase catalytic reaction, so that the reaction may proceed at an optimum temperature in almost all the reaction tubes.

As a result of an energetic study based on the facts mentioned above and made to solve those problems, the inventors of this invention have found that a gas-phase catalytic reaction proceeds adequately if at least 20% of the reaction tubes existing in the multi-tubular reactor in which the gas-phase catalytic reaction has been caused to take place are selected, the differential pressures occurring in those reaction tubes upon passage of gas thereinto are measured, the differential pressures are compared with the average of the differential pressures occurring in reaction tubes prior to the gas-phase catalytic reaction upon passage of the same kind of gas thereinto at the same flow rate (average initial differential pressure) to separate any reaction tube showing an abnormal differential pressure and adequate treatment is given to every separated reaction tube, such as changing its catalyst. Based on this finding, the inventors have completed this invention.

According to this invention, therefore, there is provided a maintaining method having the features as set forth below and attaining the object of this invention as stated above.

1. A method of maintaining a multi-tubular reactor packed with a catalyst, characterized by:

(1) selecting arbitrarily reaction tubes amounting to at least 20% of the reaction tubes in the multi-tubular reactor;

(2) passing gas into each of the selected reaction tubes to measure a differential pressure occurring in each selected reaction tube;

(3) comparing the differential pressure at (2) above with the average of differential pressures occurring in reaction tubes packed with an fresh catalyst of the same kind when passing the same kind of gas as at (2) above at the same flow rate (average initial differential pressure) to separate any reaction tube showing an abnormal differential pressure; and (4) giving adequate treatment to the separated reaction tube.

2. The method of maintaining a multi-tubular reactor as set forth at 1 above, characterized in that when the number of the reaction tubes in which the abnormal differential pressure has been measured among the arbitrarily selected reaction tubes is 5% or more of the selected reaction tubes, more reaction tubes are so selected from the reactor that the total number of the selected reaction tubes may amount to at least 80% of all the reaction tubes.

3. The method of maintaining a multi-tubular reactor as set forth at 1 above, characterized in that the abnormal differential pressure is a differential pressure 1.5 times the average initial differential pressure or higher.

4. The method of maintaining a multi-tubular reactor as set forth at 1 above, characterized in that the average initial differential pressure is the average of the initial differential pressures of 10 or more reaction tubes packed with the fresh catalyst of the same kind.

5. The method of maintaining a multi-tubular reactor as set forth at 1 above, characterized in that the adequate treatment is the changing of the catalyst in the reaction tube.

6. The method of maintaining a multi-tubular reactor as set forth at 1 above, characterized in that the adequate treatment is the plugging of the reaction tube.

7. The method of maintaining a multi-tubular reactor as set forth at 6 above, characterized in that the plugging of the reaction tube is carried out to the extent that the number of plugged reaction tubes does not exceed 30% of the total number of the reaction tubes.

8. The method of maintaining a multi-tubular reactor as set forth at 1 above, characterized in that the maintenance of the multi-tubular reactor is carried out when the gauge pressure of a raw material gas supplied for the continuous operation of the reactor has increased by a specific ratio over the value at the start of the operation.

9. The method of maintaining a multi-tubular reactor as set forth at 8 above, characterized in that the specific ratio is 1.1 times.

10. The method of maintaining a multi-tubular reactor as set forth at 1 above, characterized in that the catalyst is an oxidation catalyst.

11. The method of maintaining a multi-tubular reactor as set forth at 1 above, characterized in that the catalyst has a spherical, columnar, ring or irregular shape.

12. The method of maintaining a multi-tubular reactor as set forth at 1 above, characterized in that the multi-tubular reactor is used for a gas-phase catalytic oxidation reaction.

13. The method of maintaining a multi-tubular reactor as set forth at 12 above, characterized in that the gas-phase catalytic oxidation reaction is the gas-phase catalytic oxidation reaction of propane, propylene or isobutylene.

BEST MODE OF CARRYING OUT THE INVENTION

The invention will now be described in further detail.

The multi-tubular reactor to which this invention pertains usually contains several thousand to several tens of thousand reaction tubes as stated before, and moreover, the reaction tubes showing an abnormal differential pressure, as thereby causing coking (hereinafter sometimes referred to as abnormal reaction tubes) are scattered in the multi-tubular reactor and exist without showing any tendency at those sites in the reactor which cannot be explained by the flow of reaction gas or the flow of a heat medium.

The maintenance of such a multi-tubular reactor is perfect if the catalyst in all of its reaction tubes is changed to a fresh catalyst, but it means changing the catalyst not only in any such abnormal reaction tube, but also in a rather large number of still useful reaction tubes, leading to an unnecessary increase of work and a large loss of catalyst.

This invention has been made to avoid any such increase of cost and is more specifically started by selecting reaction tubes amounting to at least 20% of the reaction tubes in a multi-tubular reactor. The selection of reaction tubes is preferably made by random sampling from the whole multi-tubular reactor. Gas is passed through every selected reaction tube at a specific flow rate, such as a flow rate of, for example, 1500 Nl/hr which is actually adopted for a gas-phase catalytic reaction employing the multi-tubular reactor to measure the differential pressure occurring in each reaction tube and the value thereof is compared with the average of differential pressures occurring in a given number of reaction tubes packed with a given catalyst when gas is passed through each reaction tube at the same flow rate (average initial differential pressure), whereby an abnormal reaction tube or tubes are separated. The number of the reaction tubes of which the initial differential pressures are measured is not necessarily limited, but it is preferable to use, for example, 10 or more unused reaction tubes. It is desirable to determine the average initial differential pressure beforehand and it is also possible to use the average initial differential pressure of all the unused reaction tubes in the multi-tubular reactor to be maintained, as determined prior to the start of its use.

Every reaction tube showing an abnormal differential pressure, for example, 1.5 times the average initial differential pressure or higher, or twice or higher under certain circumstances, or sometimes thrice or higher, is separated from the selected reaction tubes and subjected to treatment, but if the number of the abnormal reaction tubes is 5% or more of the selected reaction tubes, an abnormal reaction tube or tubes other than the selected reaction tubes are very likely to exist and it is preferable to select more reaction tubes so that the selected reaction tubes may amount to at least 80% of the reaction tubes. Differential pressures are likewise measured of all of the newly selected reaction tubes and every reaction tube showing an abnormal differential pressure is likewise separated.

The method of measuring a differential pressure is not particularly limited, but it is possible to mention, for example, a method in which gas is passed through a reaction tube at a fixed flow rate by a mass flow meter and its pressure is measured. The gas passed through the reaction tube is not particularly limited, but air is desirable for safety reasons and its flow rate is desirably a flow rate which will prevail during the steady state of an actual reaction.

The reaction tubes as separated are each given specific treatment. The specific treatment given to the reaction tube is preferably the changing of the catalyst in every abnormal reaction tube or its plugging.

The changing of the catalyst may be carried out by any method that is usually employed for the renewal of the catalyst in any reaction tube.

The removal of the catalyst from any abnormal reaction tube may be carried out by any customary method. When any abnormal reaction tube shows only a low degree of coking, etc., it is possible to remove the catalyst relatively easily by taking off the catalyst retainer at the bottom of the reaction tube, but as any reaction tube shows a higher degree of coking, etc., the catalyst is removed by imparting ultrasonic or other vibration to the reaction tube, or by scraping out by any ordinary device if required.

The method of packing a reaction tube with a catalyst is not particularly limited, either, but it may be carried out by any common method. The reaction tube usually has a catalyst retainer at its bottom and is packed with a catalyst through its top.

However, while an extrusion, tablet compression or otherwise molded product of a powdery catalyst, such as a molybdenum and bismuth-based composite oxide catalyst, is preferably used as an oxidation catalyst for a gas-phase catalytic oxidation reaction as will be stated later, a molded catalyst is relatively brittle against an external force and is easily broken into a powder by an impact of packing. An increase of a broken catalyst presents the problem of a rising differential pressure in the reaction tube.

As methods of suppressing the breakage and powdering of a catalyst during its packing, there are, for example, (1) A method employing a depolymerizable organic high molecular compound for coating a catalyst surface to improve the mechanical strength of the catalyst (Japanese Patent No. 2,852,712);

(2) A method employing a string-like substance placed in a reaction tube and having a shape and a thickness not substantially obstructing any falling catalyst when the catalyst is dropped through the top of the reaction tube to pack it (JP-A-5-31351);

(3) A method in which a reaction tube is filled with dry ice before a catalyst is dropped to pack it, then it is packed with the catalyst and the dry ice is removed by vaporization (JP-A-10-277381);

(4) A method in which a reaction tube is filled with a liquid substance before a catalyst is dropped to pack it, then it is packed with the catalyst and the liquid substance is removed (JP-A-9-141084);

(5) A method using an automatic packing machine having a catalyst feed conveyor allowing the control of the catalyst packing time (JP-A-11-333282), and any of these methods or any adequate combination thereof may be used for packing a reaction tube with a catalyst in accordance with this invention.

The plugging of an abnormal reaction tube is the treatment done to stop the flow of any reactant raw material gas into any abnormal reaction tube by putting a plug therein, thereby making it possible to prevent any abnormal reaction, such as a side reaction, in the abnormal reaction tube to thereby prevent any lowering in the selectivity of the main reaction.

The method of plugging a reaction tube is not particularly limited. For example, it is possible to mention such a method as filling a reaction tube with any substance not participating in the reaction, closing it with heat-resistant putty, or driving in a wedge and closing any clearance with putty. If the flow of gas is not stopped completely, however, it is preferable to adopt a plugging method as described below, so that no raw material gas may pass in its unreacted form. It is possible to mention, for example, a method including forming a layer of glass wool on the catalyst layer in a separated abnormal reaction tube, forming a layer of fine particles thereon, forming another layer of glass wool thereon and finally closing the opening of the reaction tube tightly with a metallic cap. In the case of, for example, a reaction tube having a diameter of 25 to 50 mm and a length of 3 to 4 m, the first layer of glass wool on the catalyst layer may usually have a thickness of about 30 mm and the second layer of glass wool on the layer of fine particles may usually have a thickness of about 20 mm. The fine particles are preferably a crushed product of the same catalyst as that with which the reaction tube is packed, and the layer of fine particles may have a thickness differing with the diameter of those particles, typically for example, a thickness of 120 mm or more when the particle diameter is 75 μm or less, a thickness of 210 mm or more when the particle diameter is from 106 to 500 μm, or a thickness of 760 mm or more when the particle diameter is from 500 to 1000 μm. The layer of fine particles formed between the catalyst layer and the cap when plugging the reaction tube is intended for reacting any reactant raw material gas leaking into the reaction tube despite its plugging. This disables any raw material gas to pass through the reaction tube in its unreacted state.

If the quantity of the plugged reaction tubes is too large, the corresponding decrease in the number of the effective reaction tubes brings about a lowering in the rate of conversion and the resulting excess of the burden bearing on the effective reaction tubes accelerates the deterioration of the catalyst in the normal reaction tubes, and it is, therefore, preferable for the quantity of the plugged reaction tubes to fall within a range not exceeding 30%, or more preferably not exceeding 20%, of the reaction tubes in the multi-tubular reactor.

The treatment of abnormal reaction tubes may also be carried out by combining appropriately the changing of the catalyst in any such reaction tube and the plugging of any reaction tube.

Description will now be made of the manufacture of (meth) acrolein and (meth)acrylic acid by the gas-phase catalytic oxidation reaction of propene, propylene or isobutylene as a typical gas-phase catalytic reaction carried out by using a multi-tubular reactor to which this invention pertains.

This reaction usually employs a method including a former stage of reaction for oxidizing propane, propylene or isobutylene in the presence of a molybdenum and bismuth-based composite oxide catalyst as an oxidation catalyst to manufacture mainly (meth)acrolein and a latter stage of reaction for oxidizing (meth)acrolein, product of the former stage of reaction, in the presence of a molybdenum-vanadium composite oxide catalyst to manufacture (meth)acrylic acid.

Typical systems for an industrialized gas-phase catalytic oxidation reaction are a one-pass system, an unreacted propylene (or isobutylene) recycle system and a waste combustion gas recycle system.

The one-pass system is a method in which a mixture of propylene (or isobutylene), air and steam is supplied through the inlets for a reactant raw material gas of the reaction tubes in a multi-tubular reactor for the former stage of reaction and converted mainly to (meth)acrolein and (meth)acrylic acid during the former stage of reaction, while the outlet gases thereof are not separated from the products thereof, but are supplied to the reaction tubes in a multi-tubular reactor for the latter stage of reaction to have (meth)acrolein oxidized into (meth)acrylic acid. In this connection, it is common to supply the latter stage of reaction with any air and steam as required for the latter stage of reaction in addition to the outlet gases of the former stage of reaction.

The unreacted propylene (or isobutylene) recycle system is a method in which gases containing (meth)acrylic acid obtained as a reaction product at the outlet of the latter stage of reaction are guided to a unit for collecting (meth)acrylic acid, in which (meth)acrylic acid is collected as an aqueous solution, and a part of waste gases containing unreacted propylene (or isobutylene) are supplied from the collecting unit to the inlet for a reactant raw material gas for the former stage of reaction, whereby a part of unreacted propylene (or isobutylene) is recycled.

The combustion waste gas recycle system is a method in which gases containing (meth)acrylic acid obtained as a reaction product at the outlet of the reactor for the latter stage of reaction are guided to a unit for collecting (meth)acrylic acid, in which (meth)acrylic acid is collected as an aqueous solution, all the waste gases from the collecting unit are catalytically combusted and oxidized, so that the unreacted propylene, etc. which they contain may be converted to mainly carbon dioxide and water, and a part of the resulting combustion waste gases are supplied to the inlet for a reactant raw material gas for the former stage of reaction.

An oxidation catalyst represented by composition formula (1) below can be mentioned as the catalyst used in the former stage of reaction for the gas-phase catalytic oxidation reaction:

$$Mo_aW_bBi_cFe_dA_eD_fE_gG_hJ_iO_x \qquad (1)$$

where Mo, W, Bi, Fe and O stand for the elements represented by those symbols, respectively; A stands for at least one kind of element selected from cobalt and nickel; D stands for at least one kind of element selected from sodium, potassium, rubidium, cesium and thallium; E stands for at least one kind of element selected from alkaline earth metals; G stands for at least one kind of element selected from phosphorus, tellurium, antimony, tin, cerium, lead, niobium, manganese, arsenic, boron and zinc; J stands for at least one kind of element selected from silicon, aluminum, titanium and zirconium; a, b, c, d, e, f, g, h, i and x stand for the atomic ratios of the elements, respectively; when a is 12, b is 0 to 10, c is 0 to 10 (preferably 0.1 to 10), d is 0 to 10 (preferably 0.1 to 10), e is 0 to 15, f is 0 to 10 (preferably 0.001 to 10), g is 0 to 10, h is 0 to 4 and i is 0 to 30, while x is a value depending on the oxidation states of the elements.

An oxidation catalyst represented by composition formula (2) below can be mentioned as the catalyst used in the latter stage of reaction for the gas-phase catalytic oxidation reaction:

$$Mo_aV_bW_cCu_dQ_eZ_fO_x \qquad (2)$$

where Mo, V, W, Cu and O stand for the elements represented by those symbols, respectively; Q stands for at least one kind of element selected from magnesium, calcium, strontium and barium; Z stands for at least one kind of element selected from titanium, zirconium, cesium, chromium, manganese, iron, cobalt, nickel, zinc, niobium, tin, antimony, lead and bismuth; a, b, c, d, e, f and x stand for the atomic ratios of the elements, respectively; when a is 12, b is 0 to 14, c is 0 to 12, d is 0 to 6, e is 0 to 3 and f is 0 to 3, while x is a value depending on the oxidation states of the elements.

These catalysts can be prepared by, for example, the method described in JP-A-63-54942.

According to this invention, the catalyst may be a molded catalyst formed by extrusion or tablet compression molding, or a supported catalyst formed by having a composite oxide composed of a catalytic component and carried on an inert support, such as silicon carbide, alumina, zirconium oxide or titanium oxide. It is not particularly limited in shape, either, but may be of any shape, such as spherical, columnar, ring, star or irregular, though a ring-shaped catalyst is, among others, preferred for its effectiveness in preventing the accumulation of heat at any hot spot.

Moreover, the catalyst for use in the invention may be an independent one, or one diluted with an inert substance. The inert substance may be any material remaining stable under the conditions under which reaction products, such as (meth)acrolein and (meth)acrylic acid, are formed, and not reactive with any starting substance, such as olefin, or any product, such as unsaturated aldehyde or unsaturated fatty acid, and more specifically any substance used as a support for the catalyst, such as alumina, silicon carbide, zirconium oxide or titanium oxide. Its shape is not limited, as that of the catalyst is not, but any shape, such as spherical, columnar, ring, flaky, net or irregular, may be acceptable. The inert substance is used to adjust the activity of the catalyst as a whole in a catalyst-packed layer to prevent any abnormal generation of heat during an exothermic reaction.

The amount of the inert substance to be used depends on the catalyst activity as intended, but it is, for example, preferable to divide the catalyst-packed layer in a reaction tube and increase the amount of the inert substance in the vicinity of the inlet for a reactant raw material gas to lower the catalyst activity and suppress the reaction, while in the vicinity of the reaction gas outlet, the amount of the inert substance is decreased to raise the catalyst activity and promote the reaction.

In the context of this invention, the multi-tubular reactor is not particularly limited, but may be any one that is generally used on an industrial basis.

The timing at which the maintenance of a reactor is carried out in accordance with the method of this invention for maintaining a multi-tubular reactor is not necessarily limited, but it may be carried out on the occasion of usual regular repair, or at specific intervals of time during continuous operation, or when the gauge pressure of raw material gas supply has increased during continuous operation by a specific ratio over the value at the start of the operation. The intervals at which maintenance including the maintenance according to this invention is carried out depend on the conditions of the apparatus and its operation, but an interval of, for example, every 10,000 or 8,000 hours is generally selected. When the interval is dictated by an increase of the gauge pressure, the specific ratio of the increase of the gauge pressure dictating it depends on the conditions of the apparatus and its operation, but it is generally at the time of an increase by, for example, 1.1 times over the value at the start of operation.

EXAMPLES

The invention will now be described more specifically by examples.

(Preparation of a Catalyst)

94 parts by weight of ammonium paramolybdate were dissolved in 400 parts by weight of pure water under heat. On the other hand, 7.2 parts by weight of ferric nitrate, 25 parts by weight of cobalt nitrate and 38 parts by weight of nickel nitrate were dissolved in 60 parts by weight of pure water under heat. These solutions were mixed under thorough stirring to give a solution like slurry.

Then, 0.85 part by weight of borax and 0.36 part by weight of potassium nitrate were dissolved in 40 parts by weight of pure water under heat, the resulting solution was added to the above slurry and 64 parts by weight of granular silica were, then, added thereto under stirring. Then, 58 parts by weight of bismuth subcarbonate to which 0.8% by weight of magnesium had been compounded were admixed with the slurry under stirring and after the mixture was dried under heat, it was treated at 300° C. for an hour in an air atmosphere, the resulting granular solid was subjected to tablet compression by a molding machine to form columnar tablets having a diameter of 5 mm and a height of 4 mm and they were baked at 500° C. for four hours to yield a molybdenum and bismuth-based composite oxide catalyst having composition formula (3) as shown below and used for the gas-phase catalytic oxidation reaction of propylene:

$$Mo_{12}Bi_5Ni_3Co_2Fe_{0.4}Na_{0.2}Mg_{0.4}B_{0.2}K_{0.1}Si_{24}O_x \qquad (3)$$

(where x is a value depending on the oxidation states of the elements).

(Manufacture of Reaction Tubes)

Three catalyst layers were formed in a stainless steel tube having a catalyst retainer at its bottom and having an inside diameter of 25.4 mm and a length of 3.5 m by using the above catalyst having its catalytic activity adjusted by mixing silica balls having a diameter of 5 mm and not having any catalytic activity and packing it with 350 ml, 340 ml and 790 ml thereof in their order through the reactant raw material gas inlet of the reaction tube so that they might have a catalytic activity ratio of 0.5:0.7:1.

Multi-Tubular Reactor

A reactor shell (having an inside diameter of 4,500 mm) capable of accommodating 10,000 reactor tubes as described above was employed for a multi-tubular reactor.

The reaction tubes are secured by tube plates mounted in the upper and lower portions of the reactor shell and mounted in the reactor shell with their inlets for a reactant raw material gas facing upward. Between the two vertically spaced apart tube plates, there are at least two kinds of disk-shaped baffle plates, i.e. a disk-shaped baffle plate having in its center a hole in which no reaction tube is secured, and a disk-shaped baffle plate having a smaller diameter than that of the reactor shell so that when mounted in the center of the reactor shell, its outer periphery and the inner wall of the reactor shell define a clearance therebetween, which are secured to the reaction tubes, so that a heat medium may flow in a meandering way through the hole of the baffle plate and the clearance between the outer periphery and the inner wall (the openings of the baffle plates) and be thereby stirred.

A raw material gas is introduced through the raw material supply port of the reactor at its top and flows through the catalyst layers in the numerous reaction tubes to undergo a gas-phase catalytic oxidation reaction, the reaction product is collected from the bottoms of the reaction tubes into the lower portion of the reactor defined by the lowermost baffle plate and discharged through the product discharge port of the reactor at its bottom.

On the other hand, the heat medium is introduced through a heat medium inlet formed in the side wall of the reactor shell somewhat above the lower tube plate, rises among the reaction tubes, while being meandered by the baffle plates, and is discharged through a heat medium outlet, and a part thereof has its temperature regulated by a heat exchanger and is returned to the heat medium inlet.

Thermocouples for temperature measurement were one inserted in the center of each of five reaction tubes situated in typical positions radially of the reactor and having ten points of measurement along its axis and one for one-point measurement installed in the vicinity of each of the inlet and outlet for the heat medium.

(Measurement of Differential Pressure)

The average flow rate of the raw material gas flowing in each reaction tube is obtained by dividing the flow rate of the raw material gas supplied to the multi-tubular reactor under the standard reaction conditions by the number of the reaction tubes and the same amount of air as the average flow rate is passed into each reaction tube to be tested so that any resulting differential pressure may be measured.

The average initial differential pressure was obtained by calculating an average of the differential pressures occurring in ten reaction tubes having substantially the same height of the catalyst-packed layers and measured by the method as described above.

In the following examples, the raw material gas flowing in the reaction tubes had an average flow rate of 1,230 NL/hr and the reaction tubes had an average initial differential pressure of 19 kPa, as the raw material gas was supplied at a flow rate of 12,300 Nm³/hr under the standard reaction conditions.

(Calculation of Conversion Rate of Propylene and Yields of Acrolein and Acrylic Acid)

The conversion rate of propylene and the yields of acrolein and acrylic acid were calculated in accordance with the following expressions:

Conversion rate of propylene (%)=[(Amount of reacted propylene (mols))÷(Amount of propylene supplied (mols))]×100

Total yield of acrolein and acrylic acid (%)=[(Total amount of acrolein and acrylic acid produced (mols))÷(Amount of propylene supplied (mols))]×100

Example 1

The oxidation reaction of propylene was carried out by using the multi-tubular reactor as described above. The raw material gas was composed of 9 mol % of propylene, 15 mol % of oxygen, 9 mol % of steam and 67 mol % of nitrogen, and was supplied at a gauge pressure of 75 kPa (kPaG) and a feed rate of 12,300 Nm³/hr. A molten mixture of nitrates (niter) was used as the heat medium and its inlet temperature was set at 335° C. The catalyst layers had a maximum peak temperature of 395° C.

The reactor was operated for 8,000 hours continuously and its operation was stopped. The conversion rates of propylene and the yields of acrolein and acrylic acid at the time of the initial reaction and immediately before the stop of operation after 8,000 hours of continuous operation were as follows:

<At the Time of the Initial Reaction>
Conversion rate of propylene: 98.5 mol %
Total yield of acrolein and acrylic acid: 91.7 mol %

<After 8,000 Hours>
Conversion rate of propylene: 98.1 mol %
Total yield of acrolein and acrylic acid: 90.8 mol %

After the operation was stopped and after the heat medium was removed and the reactor was allowed to cool, 2,500 reaction tubes out of 10,000 (25% of the reaction tubes) were selected by random sampling and a different pressure occurring in each reaction tube was measured by passing air therethrough at a rate of 1,230 NL/hr. The results of the measurement revealed five reaction tubes having a differential pressure twice the average initial differential pressure or higher, 14 having a differential pressure from 1.5 times to less than twice and 2,481 having a normal range of differential pressures less than 1.5 times. A total of five reaction tubes having a differential pressure twice the average initial differential pressure or higher (0.2% of the selected reaction tubes) were separated from the rest and had the catalyst removed therefrom and were packed with a fresh catalyst.

Then, the renewed multi-tubular reactor was used for carrying out the oxidation reaction of propylene under the same conditions as stated above and for the same length of time continuously. The catalyst layers had a maximum peak temperature of 389° C. The conversion rates of propylene and the yields of acrolein and acrylic acid at the time of the initial reaction in the second time of continuous operation and after 8,000 hours of continuous operation were as follows:

<At the Time of the Initial Reaction>
Conversion rate of propylene: 98.1 mol %
Total yield of acrolein and acrylic acid: 91.0 mol %

<After 8,000 Hours of Continuous Operation>
Conversion rate of propylene: 97.6 mol %
Total yield of acrolein and acrylic acid: 85.6 mol %

The operation was stopped again and 2,500 reaction tubes were likewise selected and had their differential pressures measured. The results of the measurement revealed 130 reaction tubes having a differential pressure twice the average initial differential pressure or higher, 200 having a differential pressure from 1.5 times to less than twice and 2,170 having a normal range of differential pressures less than 1.5 times. A total of 130 reaction tubes having a differential pressure twice the average initial differential pressure or higher (5.2% of the selected reaction tubes) were separated from the rest and as the number of the separated reaction tubes was 5% or more, 6,000 more reaction tubes were selected from the reactor and likewise had their differential pressures measured.

The reaction tubes selected for the second time consisted of 330 reaction tubes having a differential pressure twice the average initial differential pressure or higher, 500 having a differential pressure from 1.5 times to less than twice and 5,170 having a normal range of differential pressures less than 1.5 times. A total of 330 reaction tubes having a differential pressure twice the average initial differential pressure or higher (5.5% of the selected reaction tubes) were separated from the rest and a total of 460 reaction tubes including the first separated ones (about 5.4% of the selected reaction tubes) had the catalyst removed therefrom and were packed with a fresh catalyst.

Then, the multi-tubular reactor as renewed again was used for carrying out the oxidation reaction of propylene under the same conditions as stated above and for the same length of time continuously. The catalyst layers had a maximum peak temperature of 383° C. The conversion rates of propylene and the yields of acrolein and acrylic acid at the time of the initial reaction in the third time of continuous operation and after 8,000 hours of continuous operation were as follows:

<At the Time of the Initial Reaction>
Conversion rate of propylene: 97.6 mol %
Total yield of acrolein and acrylic acid: 90.5 mol %
<After 8,000 Hours of Continuous Operation>
Conversion rate of propylene: 97.1 mol %
Total yield of acrolein and acrylic acid: 86.4 mol %

After the operation was stopped, 2,500 reaction tubes were likewise selected and had their differential pressures measured. The results of the measurement revealed 100 reaction tubes having a differential pressure twice the average initial differential pressure or higher, 150 having a differential pressure from 1.5 times to less than twice and 2,250 having a normal range of differential pressures less than 1.5 times.

As is obvious from the results stated above, it is possible to maintain excellent results of operation by changing only reaction tubes showing an abnormal differential pressure to fresh reaction tubes after operating a multi-tubular reactor for 8,000 hours continuously.

Example 2

After the oxidation reaction of propylene was carried out for 8,000 hours continuously by using a multi-tubular reactor as in Example 1, its operation was stopped and 2,500 reaction tubes were likewise selected and had their differential pressures measured. The results of the measurement revealed 105 reaction tubes having a differential pressure twice the average initial differential pressure or higher, 150 having a differential pressure from 1.5 times to less than twice and 2,245 having a normal range of differential pressures less than 1.5 times. The 105 reaction tubes having a differential pressure twice the average initial differential pressure or higher (4.2% of the selected reaction tubes and about 1.1% of the whole reaction tubes) were separated from the rest and plugged.

Then, the multi-tubular reactor including the plugged reaction tubes was used for carrying out the oxidation reaction of propylene under the same conditions as stated above and for the same length of time continuously. The catalyst layers had a maximum peak temperature of 391° C. The conversion rates of propylene and the yields of acrolein and acrylic acid at the time of the initial reaction in the second time of continuous operation and after 8,000 hours of continuous operation were as follows:

<At the Time of the Initial Reaction>
Conversion rate of propylene: 98.0 mol %
Total yield of acrolein and acrylic acid: 91.0 mol %

<After 8,000 Hours of Continuous Operation>
Conversion rate of propylene: 97.5 mol %
Total yield of acrolein and acrylic acid: 85.5 mol %

As is obvious, the plugging of only the reaction tubes showing an abnormal differential pressure after operating a multi-tubular reactor for 8,000 hours continuously makes it possible to maintain results of operation not substantially different from the results of Example 1 unless the number thereof is too large.

Example 3

After the second time of continuous operation in Example 2, 2,500 reaction tubes (25% of the reaction tubes) other than the plugged ones were selected by random sampling from the multi-tubular reactor and had their differential pressures measured as in Example 1. The results of the measurement revealed 140 reaction tubes having a differential pressure twice the average initial differential pressure or higher, 200 having a differential pressure from 1.5 times to less than twice and 2,160 having a normal range of differential pressures less than 1.5 times. A total of 140 reaction tubes having a differential pressure twice the average initial differential pressure or higher (5.6% of the selected reaction tubes) were separated from the rest and as the number of the separated reaction tubes was 5% or more, 6,000 more reaction tubes were taken from the reactor and likewise had their differential pressures measured.

The reaction tubes selected for the second time consisted of 330 reaction tubes having a differential pressure twice the average initial differential pressure or higher, 500 having a differential pressure from 1.5 times to less than twice and 5,170 having a normal range of differential pressures less than 1.5 times. A total of 330 reaction tubes having a differential pressure twice the average initial differential pressure or higher (5.5% of the selected reaction tubes) were separated from the rest and a total of 470 reaction tubes including the first separated ones (about 5.5% of the selected reaction tubes) were plugged. The plugging of the reaction tubes made a total of 575 plugged reaction tubes (about 5.8% of the whole reaction tubes).

Then, the multi-tubular reactor including the newly plugged reaction tubes was used for carrying out the oxidation reaction of propylene under the same conditions as stated above and for the same length of time continuously. The catalyst layers had a maximum peak temperature of 380° C. The conversion rates of propylene and the yields of acrolein and acrylic acid at the time of the initial reaction in the third time of continuous operation and after 8,000 hours of continuous operation were as follows:

<At the Time of the Initial Reaction>
  Conversion rate of propylene: 97.4 mol %
  Total yield of acrolein and acrylic acid: 90.1 mol %
<After 8,000 Hours of Continuous Operation>
  Conversion rate of propylene: 96.8 mol %
  Total yield of acrolein and acrylic acid: 85.9 mol %
  As is obvious, some increase in the number of the plugged reaction tubes led to somewhat inferior results of operation to those of Example 1.

Example 4

After the oxidation reaction of propylene was carried out for 8,000 hours continuously by using a multi-tubular reactor as in Example 1, its operation was stopped and 2,500 reaction tubes were likewise selected and had their differential pressures measured. The results of the measurement revealed seven reaction tubes having a differential pressure twice the average initial differential pressure or higher, 12 having a differential pressure from 1.5 times to less than twice and 2,481 having a normal range of differential pressures less than 1.5 times. The seven reaction tubes having a differential pressure twice the average initial differential pressure or higher (about 0.3% of the selected reaction tubes) were separated from the rest, had the catalyst removed therefrom and were packed with a fresh catalyst, and 8,000 hours of continuous operation were carried out for the second time.

The operation was stopped again and 2,500 reaction tubes were likewise selected and had their differential pressures measured. The results of the measurement revealed 155, reaction tubes having a differential pressure twice the average initial differential pressure or higher, 200 having a differential pressure from 1.5 times to less than twice and 2,145 having a normal range of differential pressures less than 1.5 times. Although the total of 155 reaction tubes having a differential pressure twice the average initial differential pressure or higher (6.2% of the selected reaction tubes) was more than 5% of the selected reaction tubes, no more reaction tubes were taken out from the reactor to have their differential pressures measured, but only the 155 reaction tubes showing a differential pressure twice or higher were separated from the rest, had the catalyst removed therefrom and were packed with a fresh catalyst.

Then, the renewed multi-tubular reactor was used for carrying out the oxidation reaction of propylene under the same conditions as stated above and for the same length of time continuously. The catalyst layers had a maximum peak temperature of 383° C. The conversion rates of propylene and the yields of acrolein and acrylic acid at the time of the initial reaction in the third time of continuous operation and after 8,000 hours of continuous operation were as follows:

<At the Time of the Initial Reaction>
  Conversion rate of propylene: 97.6 mol %
  Total yield of acrolein and acrylic acid: 87.8 mol %
<After 8,000 Hours of Continuous Operation>
  Conversion rate of propylene: 97.1 mol %
  Total yield of acrolein and acrylic acid: 83.7 mol %
  As is obvious, when only reaction tubes showing an abnormal differential pressure first are changed to fresh reaction tubes without having more reaction tubes selected for the repeated measurement of differential pressures even if more than a given number of reaction tubes selected from a multi-tubular reactor may show an abnormal differential pressure after its continuous operation for 8,000 hours, relatively good results of operation can be obtained despite some lowering of the yields as compared with Example 3 above, unless the number of the reaction tubes showing an abnormal differential pressure in their first differential pressure test is so large as to amount to, for example, 10% or more of the selected reaction tubes.

Although no data have been shown on the conversion rates as obtained from the first or second time of continuous operation, they were substantially the same as the results of the first and second times of continuous operation in Example 1.

Comparative Example 1

After the oxidation reaction of propylene was carried out for 8,000 hours continuously by using a multi-tubular reactor as in Example 1, its operation was stopped and 2,500 reaction tubes were likewise selected and had their differential pressures measured. The results of the measurement revealed 100 reaction tubes having a differential pressure twice the average initial differential pressure or higher, 155 having a differential pressure from 1.5 times to less than twice and 2,240 having a normal range of differential pressures less than 1.5 times. All the reaction tubes including those showing a differential pressure twice the average initial differential pressure or higher were returned into the multi-tubular reactor.

Then, the multi-tubular reactor including the reaction tubes showing an abnormal differential pressure was used for carrying out the oxidation reaction of propylene under the same conditions as stated above and for the same length of time continuously. The catalyst layers had a maximum peak temperature of 389° C. The conversion rates of propylene and the yields of acrolein and acrylic acid at the time of the initial reaction in the second time of continuous operation and after 8,000 hours of continuous operation were as follows:

<At the Time of the Initial Reaction>
  Conversion rate of propylene: 98.1 mol %
  Total yield of acrolein and acrylic acid: 87.4 mol %
<After 8,000 Hours of Continuous Operation>
  Conversion rate of propylene: 97.5 mol %
  Total yield of acrolein and acrylic acid: 79.0 mol %
  As is obvious, when no treatment is given to any reaction tube showing an abnormal differential pressure after the continuous operation of a multi-tubular reactor for 8,000 hours, it is impossible to expect keeping good results of operation, as a lowering of the total yields in the reactor is found in a short period of time.

Example 5

The oxidation reaction of propylene was carried out by performing Example 1 substantially, though it was when the gauge pressure for raw material gas supply reached 1.1 times the initial value, instead of after 8,000 hours of continuous operation, that continuous operation was stopped for the examination of differential pressures in reaction tubes.

After 6,000 hours of continuous operation, it was stopped, since the gauge pressure had reached 1.1 times the initial value. The conversion rates of propylene and the yields of acrolein and acrylic acid at the time of the initial reaction and after 6,000 hours of continuous operation immediately before the stop of operation were as follows:

<At the Time of the Initial Reaction>
  Conversion rate of propylene: 98.5 mol %
  Total yield of acrolein and acrylic acid: 91.7 mol %
<After 6,000 Hours>
  Conversion rate of propylene: 98.2 mol %
  Total yield of acrolein and acrylic acid: 88.3 mol %

After the operation had been stopped, 2,500 reaction tubes were selected and had their differential pressures measured, as in Example 1. The results of the measurement revealed 100 reaction tubes having a differential pressure twice the average initial differential pressure or higher, 150 having a differential pressure from 1.5 times to less than twice and 2,250 having a normal range of differential pressures less than 1.5 times. A total of 100 reaction tubes having a differential pressure twice the average initial differential pressure or higher (4.0% of the selected reaction tubes) were separated from the rest, had the catalyst removed therefrom and were packed with a fresh catalyst.

Then, the renewed multi-tubular reactor was used for carrying out the oxidation reaction of propylene continuously under the same conditions as stated above, while monitoring the gauge pressure for raw material gas supply. After 10,000 hours of continuous operation, it was stopped, since the gauge pressure had reached 1.1 times the initial value again. The conversion rates of propylene and the yields of acrolein and acrylic acid at the time of the initial reaction in the second time of continuous operation and after 10,000 hours of continuous operation immediately before the stop of operation were as follows:

<At the Time of the Initial Reaction>
 Conversion rate of propylene: 98.2 mol %
 Total yield of acrolein and acrylic acid: 91.0 mol %

<After 10,000 Hours of Continuous Operation>
 Conversion rate of propylene: 97.5 mol %
 Total yield of acrolein and acrylic acid: 86.0 mol %

After the operation had been stopped, 2,500 reaction tubes were likewise selected and had their differential pressures measured. The results of the measurement revealed 123 reaction tubes having a differential pressure twice the average initial differential pressure or higher, 211 having a differential pressure from 1.5 times to less than twice and 2,166 having a normal range of differential pressures less than 1.5 times.

As is obvious from the above results, it is possible to maintain good results of operation by stopping the continuous operation of a multi-tubular reactor when the gauge pressure for raw material gas supply has reached 1.1 times the initial value, measuring the differential pressures of reaction tubes in the reactor and changing only reaction tubes showing an abnormal differential pressure to fresh reaction tubes.

While the invention has been described in detail and with reference to specific embodiments thereof, it will be apparent to one skilled in the art that various changes and modifications can be made therein without departing from the spirit and scope thereof.

This application is based on Japanese patent application filed on May 31, 2004 (Patent Application No. 2004-161314), the entire contents thereof being hereby incorporated by reference.

INDUSTRIAL APPLICABILITY

The maintenance and inspection in operation of a multi-tubular reactor used for carrying out a gas-phase catalytic reaction, while supplying a reactant raw material gas, in accordance with the method of maintenance of this invention makes it possible to suppress any difference in reaction from one reaction tube to another, improve the life of a catalyst in the reactor as a whole and manufacture acrolein, acrylic acid, etc. at a high conversion rate, a high yield and a high selectivity.

The invention claimed is:

1. A method of maintaining a multi-tubular reactor packed with a catalyst, characterized by:
 (1) selecting arbitrarily reaction tubes amounting to at least 20% of the reaction tubes in the multi-tubular reactor;
 (2) passing gas into each of the selected reaction tubes to measure a differential pressure occurring in each reaction tube;
 (3) comparing the differential pressure at (2) above with the average of differential pressures occurring in reaction tubes packed with an fresh catalyst of the same kind when passing the same kind of gas as at (2) above at the same flow rate (average initial differential pressure) to separate any reaction tube showing an abnormal differential pressure; and
 (4) giving adequate treatment to the separated reaction tube.

2. The method of maintaining a multi-tubular reactor as claimed in claim 1, characterized in that the abnormal differential pressure is a differential pressure 1.5 times the average initial differential pressure or higher.

3. The method of maintaining a multi-tubular reactor as claimed in claim 1, characterized in that the adequate treatment is the changing of the catalyst in the reaction tube.

4. The method of maintaining a multi-tubular reactor as claimed in claim 1, characterized in that the adequate treatment is the plugging of the reaction tube.

5. The method of maintaining a multi-tubular reactor as claimed in claim 4, characterized in that the plugging of the reaction tube is carried out to the extent that the number of plugged reaction tubes does not exceed 30% of the total number of the reaction tubes.

6. The method of maintaining a multi-tubular reactor as claimed in claim 1, characterized in that the maintenance of the multi-tubular reactor is carried out when the gauge pressure of a raw material gas supplied for the continuous operation of the reactor has increased by a specific ratio over the initial value at the start of the operation.

7. The method of maintaining a multi-tubular reactor as claimed in claim 1, characterized in that the catalyst is an oxidation catalyst.

8. The method of maintaining a multi-tubular reactor as claimed in claim 1, characterized in that the catalyst has a spherical, columnar, ring or irregular shape.

9. The method of maintaining a multi-tubular reactor as claimed in claim 1, characterized in that the multi-tubular reactor is used for a gas-phase catalytic oxidation reaction.

10. The method of maintaining a multi-tubular reactor as claimed in claim 9, characterized in that the gas-phase catalytic oxidation reaction is the gas-phase catalytic oxidation reaction of propane, propylene or isobutylene.

* * * * *